United States Patent
Gärdin et al.

(10) Patent No.: US 6,646,734 B1
(45) Date of Patent: Nov. 11, 2003

(54) METHOD AND AN ARRANGEMENT FOR INSPECTION OF AND MEASURING AT AN OBJECT

(75) Inventors: Lars Gärdin, Västerås (SE); Peder Hellberg, Ramnäs (SE)

(73) Assignee: Westinghouse Atom AB, Västerås (SE)

( * ) Notice: Subject to any disclaimer, the term of this patent is extended or adjusted under 35 U.S.C. 154(b) by 0 days.

(21) Appl. No.: 10/049,159

(22) PCT Filed: Jul. 14, 2000

(86) PCT No.: PCT/SE00/01488
§ 371 (c)(1),
(2), (4) Date: May 3, 2002

(87) PCT Pub. No.: WO01/11632
PCT Pub. Date: Feb. 15, 2001

(30) Foreign Application Priority Data

Aug. 11, 1999 (SE) ................................................ 9902871

(51) Int. Cl.$^7$ ................................................ G01N 21/00
(52) U.S. Cl. ................................................ 356/237.2
(58) Field of Search ........................... 356/237.1–237.3

(56) References Cited

U.S. PATENT DOCUMENTS

| | | | | |
|---|---|---|---|---|
| 3,907,438 A | * | 9/1975 | Holeman | 356/601 |
| 4,377,238 A | * | 3/1983 | Wilks et al. | 209/587 |
| 4,410,278 A | * | 10/1983 | Makihira et al. | 356/445 |
| 5,063,780 A | | 11/1991 | Landry et al. | |
| 5,108,693 A | * | 4/1992 | Landry et al. | 376/245 |
| 5,156,636 A | * | 10/1992 | Kuljis | 73/597 |
| 5,418,823 A | * | 5/1995 | Kervinen et al. | 376/245 |
| 5,912,934 A | * | 6/1999 | Acks et al. | 376/248 |
| 5,991,017 A | | 11/1999 | Clark | |

FOREIGN PATENT DOCUMENTS

| | | |
|---|---|---|
| EP | 0 410 580 A2 | 1/1991 |
| EP | 0 467 211 A2 | 1/1992 |
| JP | 2173563 A | 7/1990 |

* cited by examiner

Primary Examiner—Michael P. Stafira
(74) Attorney, Agent, or Firm—Swidler Berlin Shereff Friedman, LLP

(57) ABSTRACT

A method and an arrangement for inspection of a test object (1) for stains or pits at its surface and measuring of any stain or pit, where the test object is arranged in an inspection fixture (3) in at least one defied position. A monitoring device (7) and a scanning device (5) are arranged at the inspection fixture and a control unit (9) for controlling the inspection is included in the arrangement. The surface of the test object is monitored by means of the monitoring device (7) and an image, produced by the monitoring device is shown at the control unit. A stain or pit shown by the monitoring device is subsequently scanned by mean of the scanning device and the depth or width of the stain or pit is calculated, dependent of the results of the scanning device.

12 Claims, 3 Drawing Sheets

METHOD AND AN ARRANGEMENT FOR INSPECTION OF AND MEASURING AT AN OBJECT

TECHNICAL FIELD

The invention relates to a method and an arrangement for inspection of a test object for conspicuous stains or pits and measurement of any stains or pits. The method and arrangement are especially suitable for inspection and measurement in a radiated environment. The method and arrangement are especially suitable for stains or pits as fretting marks on a nuclear fuel rod.

BACKGROUND ART

A fuel assembly for a boiling water reactor (BWR) comprises an elongated tubular container, often with rectangular or square cross section, which is open at both ends forming a continuous flow passageway. A coolant, for example water, is arranged to flow through the container. The fuel assembly comprises a large number of elongated tubular fuel rods, arranged in parallel in a certain, normally symmetrical pattern. Each of the fuel rods comprises a long tubular outer cover, named cladding, which is filled with nuclear fuel, for example in the form of pellets. The fuel rods are normally arranged vertically and retained at the top by a top tie plate and at the bottom by a bottom tie plate. Between the top tie plate and the top of the fuel rods is some play, to compensate for changes of length due to temperature changes under operation. To allow the coolant to flow freely past the fuel rods, the fuel rods are spaced from each other and prevented from bending or vibrating when the reactor is in operation by means of a plurality of spacers. The spacers are arranged at several levels in the fuel assembly, between the top and bottom plates.

A fuel assembly for a pressurised water reactor (PWR) is designed in substantially the same way as the fuel assembly for a BWR, apart from the fact that the fuel rods are not enclosed by any tubular container and the number of fuel rods is larger.

A typical spacer comprises two grids arranged in parallel and spaced apart from each other and surrounded by a common rim. Resilient material strips are arranged between the two grids forming cells. The fuel rod is guided by the strips and the cells in the grids. A plurality of supporting embossments is arranged at the grids and the strips. The embossments are normally arranged in contact with the fuel rod cladding in order to position the fuel rod.

Areas at which the spacers are in contact with the fuel rod cladding are the most likely areas for wear, as for example corrosion or abrasion, at a fuel rod. The wear often appears first in a change of colour as a conspicuous stain. When the wear of the material increases, the stains become pitted. In extreme cases pits may become so deep that the cladding becomes porous and fissile material leaks into the coolant, which should be avoided. Pits or stains on nuclear fuel rods are often referred to as fretting marks.

It is of interest to know if and in such case how the fuel rods are affected with wear or corrosion, after some time of operation in the nuclear reactor, for example to avoid leaking fuel rods. This is specially of interest when a new kind of fuel rods is brought into service, or a known sort of fuel rods is used under changed operating conditions. Fuel rods which possibly failed during operation should also be examined. If such a fuel rod is inspected, inspection is made visually, for example by means of a camera. Visual inspection is time-consuming and not very accurate. During visual inspection the width of the fretting marks may be measured. If the depth of a fretting mark is to be measured this is done manually with mechanical methods. The manual measurement incorporates further, time-consuming, handling of the fuel rod.

SUMMARY OF THE INVENTION

The invention relates to a method and an arrangement for inspection of a test object for conspicuous stains or pits and measurement of any stains or pits. The method and arrangement are especially suitable for inspection and measurement in a radiated environment. The test object may be a fuel rod where stains and pits on its cladding are referred to as fretting marks. The method includes measuring of at least one dimension, such as width or depth, of a stain or pit.

The inventive method is defined in claim 1 and the inventive arrangement in claim 5.

The arrangement comprises an inspection fixture comprising a monitoring device, a scanning device and a control urut, which may be arranged at a distance from the fixture. The test object is guided in the inspection fixture and is monitored by means of the monitoring device. Signals from the monitoring device are transmitted to the control unit and shown on a monitor. Any stain or pit on the test object, shown by the monitoring device, is subsequently scanned by means of the scanning device. The scanning device may be for example an ultrasonic transducer or a laser scanner. Scanning results are transmitted to the control unit. The depth of any stain or pit relative to test object surface is subsequently calculated by means of evaluation routines implemented in the control unit. The width of any stain or pit can be calculated in a similar manner.

An advantage of the present invention is that steps of monitoring the test object by means of a monitoring device, as for example a camera, and measuring of any stain or pit are combined in one arrangement, such that the test object needs only to be handled one time under the inspection. The measuring of the depth of stains or pits is incorporated in the method.

The inspection of the test object is partly automated and is remote controlled and supervised via the control unit. The inspection of the test object, for example a radioactive fuel rod, may be made under water in, for example, a spent fuel pool. Measurement of the depth of any stain or pit is remote controlled via a control unit. By means of, for example, a readily available ultrasonic transducer or laser scanner, an accuracy of 0.05 mm or better is achieved.

Due to the partly automated and remote controlled process, is it possible to inspect a greater number of fuel rods than before in a modest time. This is an advantage, for example, where new cladding materials are tested or in cases of operation distortions due to problems with fuel rods.

BRIEF DESCRIPTION OF THE DRAWINGS

The invention will be explained in greater detail by description of embodiments with reference to the accompanying drawings, wherein.

DESCRIPTION OF THE PREFERRED EMBODIMENTS

Figure 1:
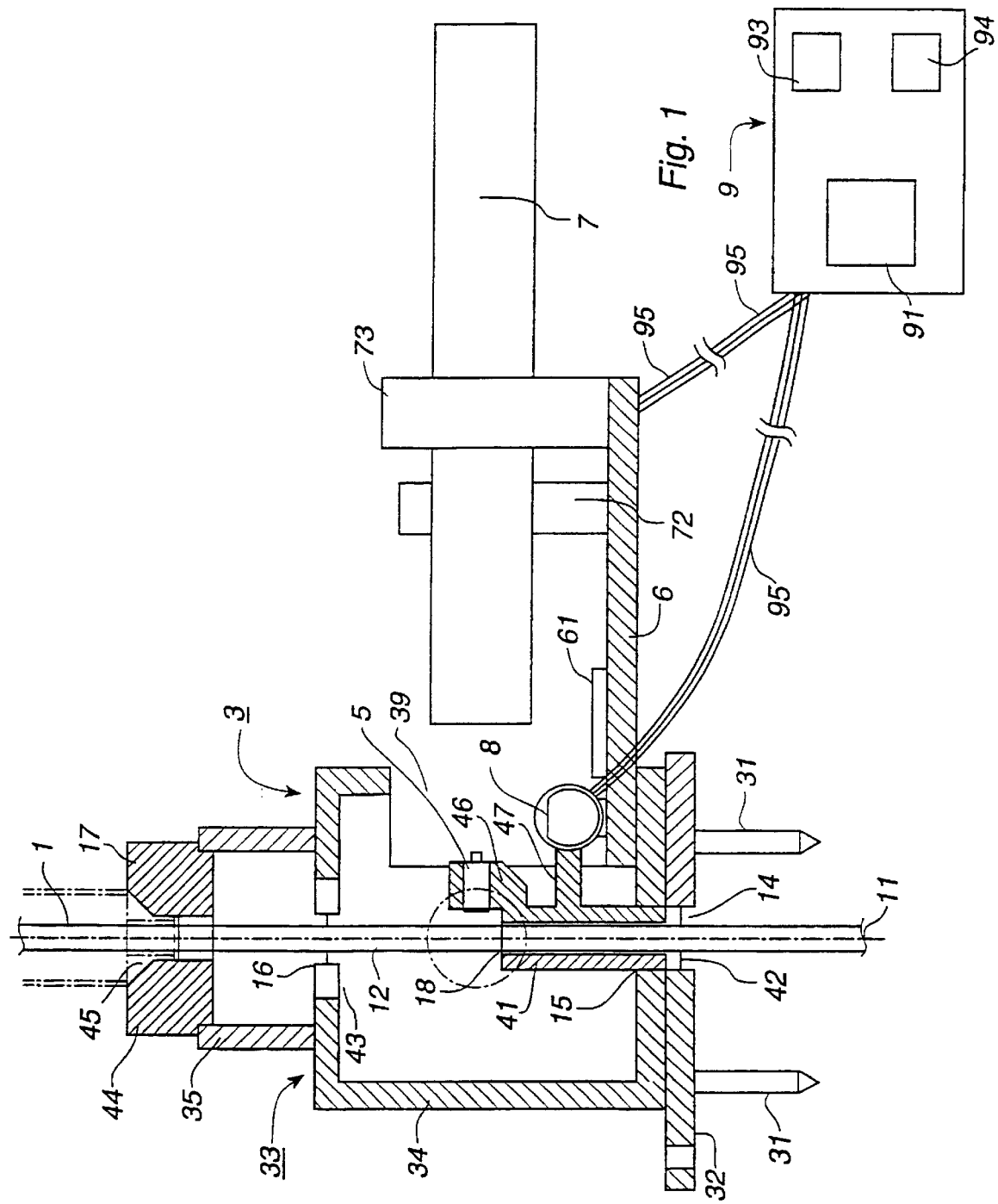
FIG. 1 shows a schematic view from the side of an inspection fixture according to the invention.
Figure 2:
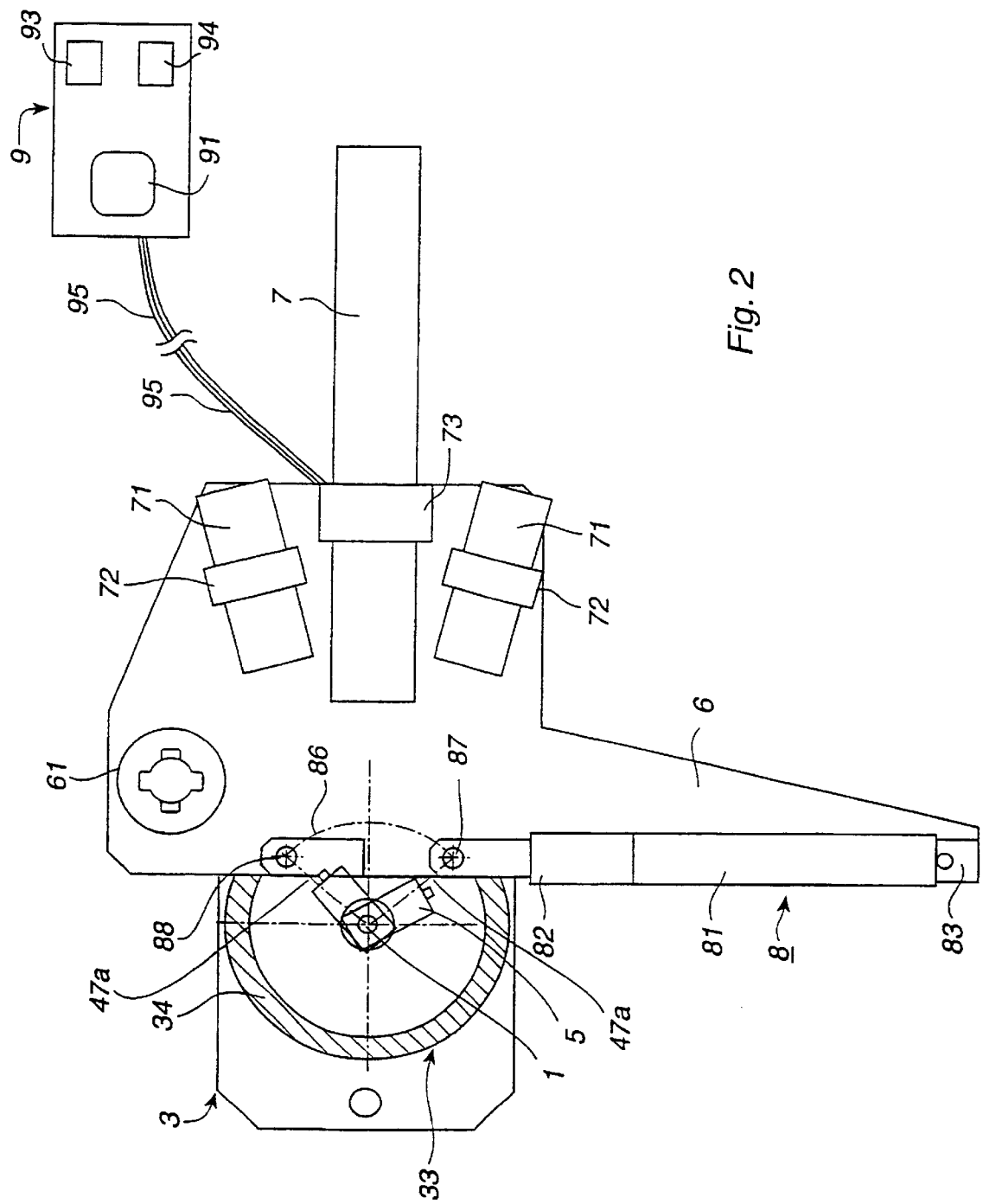
FIG. 2 shows a schematic top view of the inspection fixture of FIG. 1.

FIGS. 1 and 2 schematically show an embodiment of an inspection fixture 3 according to the invention. FIG. 1 shows the inspection fixture in a side view, partly in cross section. FIG. 2 shows a top view of the inspection fixture, partly in cross section. The inspection fixture may be mounted at a holding fixture, not shown in the figures and known per se, for example arranged in a spent fuel pool of a PWR or BWR, known per se.

The inspection fixture 3 comprises a guiding part 33, guiding a test object 1 under inspection, a monitoring device 7 in the form of a camera and a scanning device 5 in the form of an ultrasonic transducer. A control unit 9 is placed preferably at a distance from the inspection fixture 3. For an inspection taking place in, for example, a spent fuel pool, the control unit 9 is placed outside the pool, to enable supervising of the measurements. The control unit 9 comprises a display unit 91, an evaluation unit 93 and storing means 94 connected via communication means 95 to the monitoring device 7 and the scanning device 5 on the inspection fixture 3. The guiding part 33 comprises a base plate 32, a middle part 34 and an upper part 35, arranged on top of each other. The base plate 32 comprises a first opening 14. The middle part is substantially hollow-cylindrical and comprises a second opening 15 at the bottom and a third opening 16 at the top. The upper part 35 is mainly tubular formed and comprising a fourth opening 17. The openings 14, 15, 16, 17 have a common axis 11, shown in FIG. 1 as a dash-dotted line.

The middle part 34 of the guiding part 33 has a side opening 39 at a first side of the guiding part 33. A platform 6 is protruding from the opening 39 to the first side of the guiding part 33. The platform 6 is holding the monitoring device 7 and at least one lamp 71. The monitoring device 7 is facing with its optic into the side opening 39, towards the common axis 11. If a sufficiently light sensitive monitoring device 7 is used, the use of a lamp may not be necessary. A hydraulic drive 8 is arranged, partly in the side opening 39, on the platform 6.

A first centring device 43 is fitted into the third opening 16 of the middle part 34. The centring device 43 is mainly ring formed. The inner diameter of the centring device 43 corresponds to the diameter of the test object 1 with necessary play. The test object 1, guided through the openings 14, 15, 16, 17, has its longitudinal axis congruent with the common axis 11.

A second centring device 42, similar to the first centring device 43, is fitted into the first opening 14 of the base plate 32. The first 43 and the second centring 42 devices define with the diameter of their inner openings the diameter and position of a passageway 12 along the common axis 11 in the inspection fixture 3. The second 15, fourth 17 and fifth 18 opening have a diameter wider than the inner diameter of the first 43 and second 42 centring devices, to allow the test object 1 to be easily positioned in the inspection fixture 3 along the passageway 12.

A guiding sleeve 41 is fitted turnable into the second opening 15 of the middle part 34. The guiding sleeve 41 is mainly tubular formed with a fifth opening 18. The guiding sleeve 41 comprises a first extension 46 and a second extension, formed as a lever 47, perpendicular to the common axis 11. The scanning device 5 is arranged onto the first extension 46, facing with its sensor optics the surface of the test object 1. The guiding sleeve 41 with the scanning device 5 may be turned around the common axis 11, hence around the test object 1, by pushing or pulling the lever 47 by means of the hydraulic drive 8.

The upper part 35 of the guiding part 33 is mainly tubular formed and holds a leading-in sleeve 44 with a sixth opening 45. The sixth opening 45 is preferably funnel shaped. The sleeve 44 is arranged in the opening 17 in the upper part 35 to facilitate the insertion of the test object 1 through the sixth opening 45 into the passageway 12.

The inspection fixture 3 may at its base plate 32 be installed onto the holding fixture. A plurality of guiding pins 31 may therefore be arranged on one side of the base plate 32 (in the figure shown as underside). The guiding pins 31 may be fitted into corresponding openings at the holding fixture. The base plate 32 is in such case subsequently detachably fixed to the holding fixture.

The monitoring device 7 and the lamp 71 are fastened by fastening means 72, 73 to the platform 6. The monitoring device 7 may for example be a black and white tubular camera, known per se. The monitoring device 7 is arranged in its optical axis perpendicular to the common axis 11 and thereby to test object 1 surface. The scanning device 5 and the monitoring device 7 are arranged at one and the same plane. The distance of the monitoring device 7 to the common axis 11 is changeable, in order to change the size and resolution of a picture of an area inspected by the monitoring device 7.

The hydraulic drive 8 comprises a fixed part 81 and a moveable part 82, arranged telescopically in the fixed part, as shown in FIG. 2. The fixed part 81 is at a first end 83 rotatable fixed to the platform 6, whereas the driven part 82 is rotatable fixed to the lever 47, in FIG. 2 only schematically shown by dash-dotted lines 47a, marking a first and a second end position of the lever 47. By moving the driven part 82 telescopically in the fixed part 81, the lever 47 is moved. The driven part 82 is schematically shown in FIG. 2 in a first end position 87 and a second end position 88. Possible positions of a connection point of the lever 47 and the driven part 82 are schematically shown by an arc-formed dash-dotted line 86.

Figure 3:
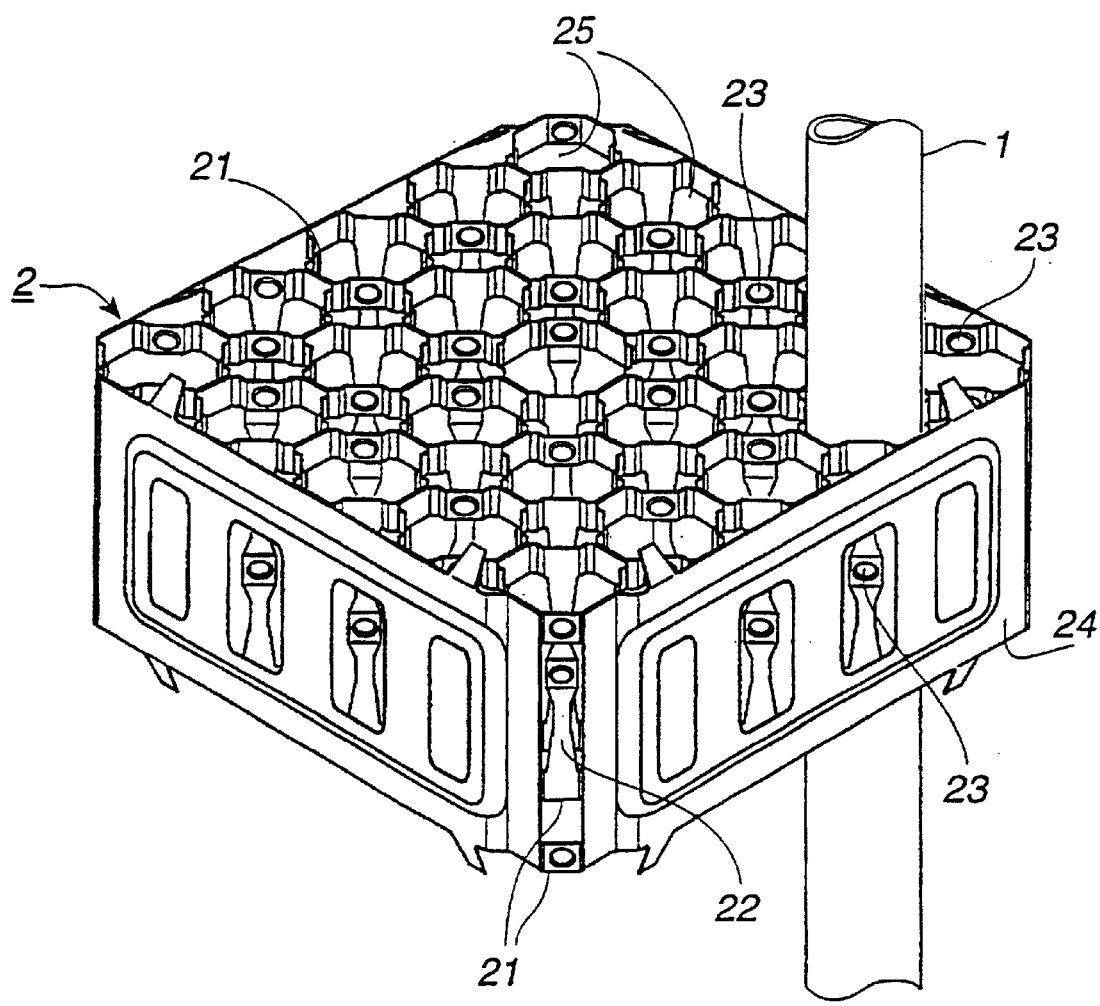
FIG. 3 shows a spacer having part of a fuel rod inserted.

FIG. 3 shows a spacer 2 having a plurality of cells 25 and a single fuel rod 1, partly shown, inserted in one of the cells 25. Normally each cell 25 surrounds an elongated element such as a fuel rod 1 or a guide tube for a control rod. For clarity a reasons FIG. 3 shows only a part of a single inserted fuel rod 1. The spacer 2 is designed to fit into a nuclear fuel assembly for a boiling water reactor (BWR). A spacer, designed for a fuel assembly for a pressurised water reactor (PWR), is designed substantially in the same way apart from the fact that the number of fuel rods is larger and thereby also the number of cells in the spacer. Spacers 2 are arranged at several levels along the fuel rods in a fuel assembly.

The exemplified spacer 2 has two grids 21 arranged in parallel and spaced apart from each other. The spacer 2 is surrounded by a rim 24 around four sides formed by open-work sheet material. Resilient strips 22 are arranged between the two grids 21. The fuel rod 1 having a cover, named cladding, is guided by the cell 25 in the form of openings in the two grids 21 and the metal strips 22. A plurality of embossments 23 are arranged at grids 21 and the metal strips 22. The embossments 23 are normally in contact with the fuel rod 1 cladding in order to position the fuel rod 1.

Location of the inspection fixture 3 as, for example, a part of the inspection and measuring arrangement in a spent fuel pool of a nuclear reactor, and control of a test object 1 as, for example, a fuel rod with the inspection and measuring arrangement according to the invention, are described in the following. The inspection is controlled by the control unit 9, placed outside the spent fuel pool.

When the inspection fixture 3 is to be installed on the holding fixture, the inspection fixture 3 is moved by means of a lifting device into the spent fuel pool. The lifting device is not shown in the figure and known per se. The lifting device is detachably fixed, in a manner known per se, into the handling opening 61 at the platform 6. The inspection fixture 3 is moved to the holding fixture, which holding fixture is arranged in the spent fuel pool, in a manner known per se. The guiding pins 31 at the base plate 3 may be fitted into corresponding openings of the holding fixture. The inspection fixture is subsequently fixed to the holding fixture, in a manner known per se.

A fuel rod 1 to be inspected is taken out of a fuel assembly by a rod-pulling tool, not shown in the figure and known per se. The fuel rod 1 is transported by means of the rod-pulling tool to the inspection fixture 3 and lowered through the sixth opening 45 into the passageway 12.

The fuel rod 1 is under the inspection procedure manipulated by the rod-pulling tool. The fuel rod 1 cladding is under the inspection procedure monitored by the monitoring device 7. By lowering the fuel rod 1, a plurality of pictures, each picture over a length and a first sector of the fuel rod 1 surface, is produced. A camera picture is displayed on the display unit 91 and stored by the storing means 93 for further evaluation. After lowering the fuel rod 1 fully, the fuel rod 1 is turned some tens of degrees around its longitudinal axis and then raised. A plurality of pictures of a second sector of the fuel rod 1 surface is produced, displayed and stored. This procedure is repeated until the whole surface or the whole area of interest of the fuel rod 1 is inspected. If during this inspection a conspicuous stain or a pit is shown at the display unit 91, the fuel rod 1 is stopped at its position, and, by means of the scanning device 5, a scan of the stain or pit is taken.

While taking a scan of a part of the fuel rod 1, the driven part 82 of the hydraulic drive 8 is moved and with this the lever 47 and subsequently the scanning device 5 in an arc-formed movement around the fuel rod 1 at the position of a stain or pit. The movement of the lever is limited by the first end position 87 and the second end position 88. The surface of the fuel rod 1 cladding is scanned along a line during the movement by the scanning device 5, while it is turned around the fuel rod 1. The result of the scan is shown on the display unit 92 in form of a graph. A stain with no depth on a smooth surface shows as a straight line, whereas a pit in the surface shows as a deviation of a straight line. The deviation from a straight line is proportional to the depth of the stain or pit. The width of the deviation is proportional to the width of the stain or pit. The depth or the width of the pit is calculated in the evaluation unit 94 in a manner known per se.

In order to achieve accurate measurement it is necessary to calibrate the inspection fixture 3 by means of a reference body with known dimensions, before inspecting the test object 1.

The described embodiment incorporates only one embodiment out of a plurality of possible embodiments of the invention.

The scanning device and/or the monitoring device are not necessarily arranged with their optical axes perpendicular to the longitudinal axis of the test object. Other angles than 90° are also possible.

For example, the scanning device may be a laser scanner, or may be placed in a fixed position, and the test object may be moved around its longitudinal axis during scanning.

It is possible in the scope of the invention to arrange the monitoring device 7 and the scanning device 5 at planes apart from each other, in a defined position to each other.

It is possible to move the monitoring device 7 and the scanning device 5 in a defined position to each other along the test object 1 which is at a fixed position.

The method may easily be adapted for test objects with a shape other than elongated or cylindrical.

What is claimed is:

1. A method identifying and measuring stains and pits at a surface of a test, wherein the test object is arranged underwater in an inspection fixture and a camera is arranged at the inspection fixture, the method comprising:
   monitoring the surface of the test object with the camera;
   showing at a control unit an image of the test object produced by the camera;
   supervising and controlling the inspection by means of the control unit;
   if an image produced by the camera shows a conspicuous stain or pit, scanning the conspicuous stain or pit on the test object, shown by the monitoring device, by means of a scanning device;
   producing at least one signal resulting from the scanning; and
   calculating from the signal a depth or width of the conspicuous stain or pit.

2. The method according to claim 1, wherein the test object has a longitudinal axis, the method further comprising:
   moving the test object under inspection along its longitudinal axis and along a passageway through the inspection fixture.

3. The method according to claim 1, wherein the test object has a longitudinal axis, the method further comprising:
   guiding the scanning device around the test object in a circular movement over a segment of a circumference of the test object during scanning.

4. The method according to claim 1, wherein the test object has a longitudinal axis, the method further comprising:
   turning the test object around the longitudinal axis while the scanning device is arranged in a fixed position at the inspection fixture during scanning.

5. An arrangement for underwater inspection of a test object for conspicuous stains or pits at a surface of the test object and measuring the stains or pits, the arrangement comprising:
   an inspection fixture;
   a camera carried by the inspection fixture and operative to monitor the surface of the test object;
   a control unit operative to control operation of the arrangement; and
   a scanning device arranged at the inspection fixture and operative to scan conspicuous stains or pits on the test object shown by the camera.

6. The arrangement according to claim 5, wherein the monitoring device and the scanning device each have an optical axis that is perpendicular to a longitudinal axis of the test object.

7. The arrangement according claim 5, wherein a distance between the test object and the monitoring device is variable to change the size of the area monitored by the monitoring device.

8. The arrangement according to claim 5, wherein the camera is a black and white camera.

9. The arrangement according to claim 5, wherein the scanning device is an ultrasonic transducer.

10. The arrangement according to claim 5, wherein the scanning device is a laser scanner.

11. The arrangement according to claim 5, wherein the test object is a fuel rod for a nuclear reactor.

12. The arrangement according to claim 5, wherein the control unit is arranged at a distance from the inspection fixture.

\* \* \* \* \*